(12) United States Patent
Roberto et al.

(10) Patent No.: US 8,158,111 B2
(45) Date of Patent: Apr. 17, 2012

(54) COSMETIC COMPOSITION AND A PROCESS FOR PREPARING SAID COMPOSITION

(75) Inventors: Alexandre Roberto, Jundiaí (BR); Adriano Tadeu Siqueira Jorge, São Paulo (BR); Luciana Villa Nova Silva, São Paulo (BR); Walter De Albuquerque Junior, São Paulo (BR)

(73) Assignee: Natura Cosmeticos S.A., Sao Paulo (BR)

( * ) Notice: Subject to any disclaimer, the term of this patent is extended or adjusted under 35 U.S.C. 154(b) by 600 days.

(21) Appl. No.: 11/917,271

(22) PCT Filed: Sep. 7, 2006

(86) PCT No.: PCT/BR2006/000181
§ 371 (c)(1),
(2), (4) Date: Sep. 19, 2008

(87) PCT Pub. No.: WO2007/028224
PCT Pub. Date: Mar. 15, 2007

(65) Prior Publication Data
US 2009/0286749 A1    Nov. 19, 2009

(30) Foreign Application Priority Data
Sep. 9, 2005  (BR) .................................... 0503719

(51) Int. Cl.
*A61Q 19/00* (2006.01)
*A61K 8/02* (2006.01)
*A61K 8/37* (2006.01)
*A61K 8/34* (2006.01)
*A61K 8/891* (2006.01)
*A61K 8/73* (2006.01)
*A61K 8/88* (2006.01)

(52) U.S. Cl. ........................................................ 424/59

(58) Field of Classification Search .................. 424/59
See application file for complete search history.

(56) References Cited

U.S. PATENT DOCUMENTS

| | | | |
|---|---|---|---|
| 7,449,203 B2 * | 11/2008 | Goldstein et al. ............. | 424/725 |
| 7,455,848 B2 * | 11/2008 | Hessefort et al. ............. | 424/401 |
| 2002/0155074 A1 | 10/2002 | Pinnell | |

FOREIGN PATENT DOCUMENTS

| | | | |
|---|---|---|---|
| EP | 1 468 668 | | 10/2004 |
| FR | 2 867 686 | | 9/2005 |
| MX | PA04 009 861 | | 4/2005 |
| MX | A-PA04009861 | * | 5/2005 |
| WO | WO 02/38109 | | 5/2002 |

OTHER PUBLICATIONS

Material Safety Data Sheet, Olivem 1000, B & T S.r.l., Jun. 19, 2002, all pages.*
Biologia & Tecnologia: "Olivem 1000: Safety Data Sheet", Jun. 19, 2002, Retrieved from Internet: http://www.essentialingredients.com/PD.
Uniqema: "The use of ARLATONE LC in personal care formulations", Jun. 2004, Research Disclosure, Mason Publications, Hampshire, GB.
PCT Search Report and Written Opinion for PCT/BR2006/000181 dated Jan. 10, 2007.

* cited by examiner

*Primary Examiner* — Johann Richter
*Assistant Examiner* — Thor Nielsen
(74) *Attorney, Agent, or Firm* — Alston & Bird LLP

(57) ABSTRACT

The present invention relates to a cosmetic composition that provides prolonged moisturizing to the skin and a differentiated sensorial, and may be employed in various types of products. This cosmetic composition comprises olive esters, biosaccharide gum-1, a wetting agent of vegetable origin, an emollient of vegetable origin, a silicone and an oiliness adsorber. Further, the present invention relates to a process of preparing this cosmetic composition.

20 Claims, No Drawings

COSMETIC COMPOSITION AND A PROCESS FOR PREPARING SAID COMPOSITION

FIELD OF APPLICATION

The present invention relates to a cosmetic composition that provides prolonged and differentiated sensorial moisturizing to the skin and can be employed in various types of products.

Further, the present invention relates to a process of preparing this cosmetic composition.

DESCRIPTION OF THE PRIOR ART

At present, there is a trend to use raw materials of vegetable origin or derived from plants to replace those of mineral and animal origin traditionally used in cosmetic formulations. Such formulations exhibit properties relating to biodegradation, physicochemical properties of interest for this purpose, among others.

In addition, other characteristics of the cosmetics become quite relevant for achieving a product of high value. Today, many cosmetic products available on the market exhibit a number of sensorial aspects and post-application effects that are undesirable, for example:
1. High degree of oiliness and stickiness;
2. Difficult spreading and slow absorption;
3. Increase of the degree of oiliness and brightness of the skin;
4. Possible formation of comedones and of other adverse reactions such as sensitization and skin irritation.

These aspects and effects are due mainly to:
1. great influence of high concentrations of glycols and of emollients necessary for obtaining a high degree of objective moisturizing (measured by equipments) and subjective moisturizing (perceived in the sensation of the skin after application of the product);
2. high degree of stickiness and/or oiliness which these products present;
3. occlusive action caused either by some emollient agents or by some wetting agents (for instance, glycols) or by some mixture inherent to these preparations;
4. elimination of skin barrier structure caused by the emollients used in a large amount, with the consequent permeation of preservatives, fragrances, chemical sunscreens and various other components of the preparation through the layers of skin where they are potentially irritating.

Next, the applicant indicates some relevant prior-art documents related to the matter of the present invention.

Document JP 2004250413 discloses a preparation for personal care containing olive oil for external use, being thermostable and applied as an anti-aging product or still for the prevention of speckles, spots and sunburns. This preparation comprises L-ascorbic acid-2-O-maleic acid-[alpha]-tocoferol ester and olive oil.

Document EP 0745371 describes a cosmetic composition in the form of a paste containing wax, oil with a thickening agent and filler. The oil present in the composition in an amount of 15% to 80% may be a vegetable oil such as olive oil.

As can be seen from the description of the present invention hereinafter, no teaching of the prior art proposes advantages referring to the presence of components of vegetable origin, associated to the formation of networks of liquid crystals, resulting in a prolonged moisturizing and an ideal sensorial for any type of skin.

SUMMARY OF THE INVENTION

The present invention has the objective of providing a cosmetic composition comprising:
- olive esters, which are cetearyl olivate and sorbitan olivate;
- biosaccharide gum-1;
- at least one wetting agent of vegetable origin;
- at least one emollient of vegetable origin;
- at least one silicone;
- at least one oiliness adsorber.

The present invention further has the objective of providing a process for preparing the above-described cosmetic composition, which comprises the following steps:

a) preparing PHASE A:
Adding a wetting agent of vegetable origin, at a temperature of about 25° C., and mixing it at a frequency ranging from 20 to 2000 rpm, for a period of 3 to 10 minutes. After achieving complete solubilization and/or dispersion, heating this phase until a temperature of about 80° C. is reached.

b) preparing PHASE B
Solubilizing cetearyl olivate and sorbitan olivate, in at least one thermostable liquid emollient at a temperature of about 80° C., mixing them at a frequency ranging from 100 to 250 rpm.

c) preparing PHASE C
Promoting hot emulsification, at a temperature of about 80° C., by adding the phase B to the phase A under constant stirring of 500 to 2000 rpm.

d) preparing PHASE E
Adding to the phase C at least one oiliness adsorbing agent, at a temperature of about 55° C., mixing at a frequency of 20 to 1500 rpm for a period of 3 to 8 minutes.

e) preparing PHASE F:
Homogenizing at least one silicone with biosaccharide gum-1, at a temperature of about 25° C. at a frequency of 200 to 400 rpm;
Adding the phase F to the phase C at a temperature of about 40° C., mixing at a frequency ranging from 20 rpm to 1400 rpm until complete incorporation is achieved.

BRIEF DESCRIPTION OF THE INVENTION

The objective of the present invention is to provide a cosmetic composition that provides intensive and prolonged moisturizing to the skin. In addition, it provides a quite differentiated sensorial by virtue of the formation of an enhanced velvety film after application and may be applied in a number of products.

Further, the cosmetic composition of the present invention comprises components of exclusively vegetable origin.

DETAILED DESCRIPTION OF THE INVENTION

The present invention relates to a cosmetic composition with a base of vegetable origin, with an intensive and prolonged moisturizing power and exhibiting a quite differentiated sensorial (an enhanced velvety film after application), and which may be employed in various types of products.

Further, the present invention relates to a specific process for preparing said cosmetic composition.

In this regard, the main examples of products that can be prepared based on the cosmetic composition of the present invention are:
face moisturizers;
body moisturizers;
anti-spot preparations for day or night use;
cosmetic preparations of localized action;
  for the treatment of spots;
  for the treatment of bags under the eyes;
facial cosmetic preparations for aftershave use;
body anti-spot preparations.

Due to the combination of chemical components that will be detailed later, as well as to the process of preparing the cosmetic composition, such composition does not have the drawbacks encountered in compositions known on the market, used for similar purposes.

The cosmetic composition of the present invention has a range of advantages and characteristics desired in a cosmetic product for the skin, some of which are listed below.

1. it has stability; enables the obtainment of stable formulations;
2. it does not have a photoirritation, photosensitizing and comedogenicity potential;
3. it does not induce a skin irritation and/or sensitization process;
4. it comprises essentially components of vegetable origin, that is to say, these are natural components the chemical structure of which has not been altered;
5. it forms networks of liquid crystals, bringing about prolonged moisturizing to the skin;
6. it has a pleasant and differentiated sensorial;
7. it brings about the formation of a silky film on the skin;
8. it provides intensive moisturizing to the skin for 24 hours;
9. it is quite soft by virtue of the vegetable origin of the components;
10. it exhibits high absorption on the skin
11. spreadability to absorption on the skin is ideal.

Cosmetic Composition of the Present Invention

As said before, the cosmetic composition of the present invention comprises:
olive esters, which are cetearyl olivate and sorbitan olivate;
biosaccharide gum-1;
at least one wetting agent of vegetable origin;
at least one emollient of vegetable origin;
at least one silicone;
at least one oiliness adsorber In addition to these components, the cosmetic composition of the present invention may still comprise optional components such as chelating agent; thickening system; antioxidant component; preserving system; active ingredients and fragrance.

Further, the term "sensorial" used herein should be understood as being a set of the following characteristics: softness, smoothness, ease of spreading and sliding, absence of fatty film and brightness.

The components used in the cosmetic composition of the present invention, as well as other compounds optionally added for the purpose of exhibiting a determined property still not achieved, are described in greater detail hereinafter.

Olive Esters—Cetearyl Olivate and Sorbitan Olivate

By preference, one uses the product Olivem 1000, produced by B&T S.r.l. These esters are natural consistency agents and emollients and result in a non-ionic emulsifying system derived from olive oil.

These esters are responsible for the formation of the network of liquid crystals within the emulsion that causes the formation of a film on the skin, bringing about the prolonged moisturizing. This characteristic is potentiated when the esters are combined with other components of the cosmetic composition of the present invention.

In the preferred embodiments of the present invention, one adds cetearyl olivate and sorbitan olivate in an amount ranging from 2.0% to 10.0%, preferably about 4.0% by weigh, based on the total weight of the cosmetic composition of the present invention.

It is important to remind that the quite pleasant sensorial of the composition in question is achieved by adding at least one emollient of vegetable origin, at least one silicone and at least one oiliness adsorber that, together with the biosaccharide gum-1 and the wetting agent of vegetable origin, potentiate the action of the emulsifier, which, as already said, are the olive esters.

Biosaccharide Gum-1

This component is the preferred active for addition to the present composition, acting as a sensorial modifier, that is to say, as a skin conditioning agent.

In the preferred embodiments of the present invention, one adds biosaccharide gum-1 in an amount ranging from 3.0% to 10.0%, preferably about 8.0% by weight, based on the total weight of the cosmetic composition of the present invention.

Wetting Agent of Vegetable Origin

The function of a wetting agent in the cosmetic composition of the present invention is to promote the retention of water on the skin of the user, that is to say, to provide water to the skin and also to prevent loss of water from the skin. The wetting agent further aids in increasing the efficacy of the emollient, reduces the scaling of the skin and improves the skin sensorial.

Some examples of optional wetting agents that may be added to the cosmetic compositions of the present invention are: glycols, preferably glycerin, propyleneglycol, butyleneglycol or diethyleneglycol and combinations thereof.

In the preferred embodiments of the present invention, glycerin is added in an amount ranging from 2.0% to 25.0%, preferably from 2.0% to 10.0% by weight, based on the total weight of the cosmetic composition of the present invention.

Emollient

The function of the emollients in cosmetic compositions is to add or replace natural oils to the skin, seeking to maintain the integrity of the hydrolipid mantle of the skin. They can also act as solubilizers of sunscreens.

As additional emollients to be added to the composition of the present invention, one may use various substances of lipophilic nature and different polarities such as alcohols and fatty acids, esters, ethers, mono-, di- or triglycerides, natural or synthetic hydrocarbons, or organic carbonates and combinations thereof.

In the preferred embodiments of the present invention, preferably one adds ethers, esters and organic carbonates, more preferably dicaprylic ether, dicapryl carbonate and cetyl lactate in an amount ranging from 0.1% to 30.0% by weight, preferably from 0.5% to 15.0% by weight, based on the total weight of the cosmetic composition of the present invention.

An example of an emulsifying system that may be added to the cosmetic composition of the present invention is as follows:

| | |
|---|---|
| Cetyl lactate | 1 to 10% |
| Triglycerides of the capric and caprylic acids | 0.5 to 12% |
| Dicaprylic ether | 0.5 to 10% |
| Dicapryl carbonate | 0.5 to 12% |

Silicones

Silicones have solvent, emollient and skin conditioning properties. Some examples of optional silicones that may be added to the cosmetic compositions of the present invention are: cyclomethicones, dimethicones, dimeticonols, phenyl trimethicones, crospolymers of cyclomethicones and dimeticones, and mixtures thereof.

In the preferred embodiments of the present invention, one adds cyclomethicones and crospolymers of cyclomethicones and dimethcones in an amount ranging from 0.01% to 30.00% by weight, preferably from 0.1% to 15.0% by weight, based on the total weight of the cosmetic composition of the present invention.

An example of silicone system that may be added to the cosmetic composition of the present invention is as follows:

| | |
|---|---|
| Cyclomethicone | 0.5 to 20% |
| Crospolymer of cyclomethicone and dimethicone | 1 to 25% |
| Dimethicone | 0.1 to 5% |

Oiliness Adsorbing Agent

As an agent to modify the sensorial, that is to say, to promote oiliness adsorption, one can add to the composition several categories of substances or mixtures thereof, such as polymethyl acrylates, aluminum and magnesium silicates, polyacrylamides, modified polysaccharides, borates, silicas and talcum.

In the preferred embodiments of the present invention, one adds preferably Nylon, more preferably Nylon 12 in an amount ranging from 0.1% to 15.00% by weight, preferably from 1.0% to 8.0% by weight, based on the total weight of the cosmetic composition of the present invention.

In addition to the components mentioned above, the cosmetic composition of the present invention may further comprise compounds conventionally used in cosmetic compositions of this type and that are detailed hereinafter:

Carrier

Water is the basis of various possibilities of cosmetic compositions, acting as a carrier for the other components. The compositions of the present invention comprise water, preferably demineralized or distilled in an adequate percentage (q.s.p.) to achieve 100% of the formula, based on the total weight of the present composition. Of course, other cosmetically acceptable carriers may be used in the present invention.

Further, water may be combined with a chelating agent, which may be etidronic acid, or preferably of the group of ethylenediaminetetraacetic acid, more preferably the disodium salt of ethilenediaminetetraacetic acid.

In the preferred embodiments, disodium EDTA is added in an amount ranging from 0.05% to 0.50% by weight, based on the total weight of the composition.

Thickening Agent

The function of the thickening agent in cosmetic compositions is to maintain in suspension other components present therein, besides providing consistency thereto.

Some examples of thickening agents that may be used in the present invention are: natural polymer as alginic acid and derivatives thereof, cellulose and derivatives scleroglucanes, or preferably some type of gum such as xanthan, tara, guar or arabic, more preferably xanthan gum, and synthetic polymers that can also have the function of a polymeric emulsifier formed by polymers and carboxyvinylic copolymers, acrylates, methacrylates, alkyl acrylates, acrylamides, taurates and/or by combinations thereof, preferably the polymers and crospolymers of acrylates and acrylates of alkyl and gums.

In the preferred embodiments, one adds preferably the crospolymers of acrylates and acrylate of $C_{10-30}$ alkyl and xanthan gum in an amount ranging from 0.1% to 1.0% by weight, based on the total weight of the composition.

Skin Conditioning Agent

As conditioning agents one may use wetting agents, moisturizing agents or skin conditioning agents. Some examples of conditioning agents that may be added to the cosmetic composition of the present invention are compounds based on mono-, oligo- and polysaccharides, biopolymers of uronic acids highly sulfated polygalactosides and natural salts and/or by combinations thereof, preferably mono- and oligosaccharides and algae extracts, marine algae (*Phacophyccae* and *Rhadophyccae*) extracts and sorbitol.

Preferably, one may add a skin conditioning agent in an amount ranging from 1.0% to 30.0% by weight, preferably from 2.0% to 10.0% by weight, based on the total weight of the composition.

Antioxidant Agent

Antioxidant agents act in protecting the topical composition, preventing oxidation and incompatibilities in the formulations.

Compounds with antioxidant properties that may be added to the compositions of the present invention are: either hydrophilic or lipophilic substances or mixtures thereof, preferably lipophilic substances such as butyl hydroxyl toluene, butyl hydroxyl anisole or tetradibutyl pentaeritrityl hidroxyhydrocynnamate.

In the preferred embodiments of the cosmetic compositions of the present invention, one uses butyl hydroxyl toluene as an antioxidant agent in an amount ranging from 0.01% to 1.00% by weight, it being preferably to use an amount between 0.01% and 0.40% by weight, based on the total weight of the composition.

Preserving Agent

A preserving agent, as the name itself indicates, provides preservation of the composition to which it is added, that is to say, it provides effective protection to the composition against attach by microbial agents, increasing its useful life or shelf life.

There is a great variety of preserving agents suitable for cosmetic compositions, and all the agents that have this function may be added to the cosmetic composition of the present invention, either in isolation or in combination.

Some preferred examples of preserving agents to be added to the composition of the present invention are: mixtures of various categories of substances such as parebens, organic acids, imidazolidinyls, diazolidines, isothiazolinones, hydroxymethylglycinates, phenolic alcohols and iodo-alkyl carbamates, preferably phenolic alcohols and iodo-alkyl carbamates.

In the preferred embodiments of the present invention, one uses a preserving system that comprises phenoxyethanol and 3-iodo-2-propinylbutyl carbamate in an amount ranging from 0.01% to 5.00% by weight, preferably from 0.10% to 2.00% by weight, based on the total weight of the cosmetic composition of the present invention.

Emulsifying Agent

As emulsifying agents, one can use the anionic emulsifiers, non-anionic emulsifiers and polymeric emulsifiers.

Some examples of emulsifying agents may be added, such as: mixture of various categories of substances such as anionic, cationic, preferably non-ionic emulsifiers such as propoxy and/or ethoxilated fatty alcohols, sorbitan esters, methyl glucose, glucose propylglyceryl, fatty acids and glycols, fatty acids and sucrose, fatty acids and pentaerythritol, ethoxylated and/or non-ethoxilated, copolymers of ethylene oxide and propylene oxide, alkyl glycosides and polyglycosides, ethoxylated and/non-ethoxylated animal and vegetable steroids, preferably ethoxylated stearyl alcohols and ethoxylated esters.

In the preferred embodiments of the present invention, one adds glyceryl stearate in an amount ranging from 0.1% to 15.0% by weight, preferably from 0.2% to 8.0% by weight, based on the total weight of the cosmetic composition of the present invention.

Active Ingredient System

The active ingredient system may comprise substances of various categories such as alpha-bisabolol, alantoin, alantoin, glycirizinates, natural extracts, protein hydrolisates, peptides and polypeptides, flavonoids, steroids, vegetable oils, ceramides, oligo and polysaccharides, vitamins A, E, C and derivatives thereof.

In the preferred embodiments of the present invention, one adds preferably hydrolyzed rice protein, soybean isoflavones, Jambu extract (Spilanthes oleracea), biosaccharide gums 2 and 3, microencapsulated pure tocoferol in an amount ranging from 0.002% to 20.000% by weight, preferably from 0.05% to 10.0% by weight, based on the total weight of the cosmetic composition of the present invention.

Fragrance

In the composition of the present invention the addition of scent or fragrance selected from a possible range of substances is optional. Preferably, one adds a fragrance of the floral fresco family, more preferably Inovação Mod. AF® from Quest International. The amount of fragrance to be added to the cosmetic composition of the present invention preferably ranges from 0.01% to 6.00%, more preferably ranging from 0.05% to 2.00% by weight, based on the total weight of the composition of the present invention.

pH Adjusting Agent

In order to obtain a final composition with pH values that are neutral or suitable to the skin, one may add to the compositions of the present invention: inorganic hydroxides like sodium hydroxide, calcium carbonate, citric acid, phosphoric acid, sodium citrate, succinic acid, potassium acetate, sodium chloride, amines like tertiary amine, triethanolamine and mixtures thereof.

In the preferred embodiments of the present invention, one uses, as a pH adjusting agent, triethanolamine in an amount that varies according to the final pH of the product and according to the concentration of some polymeric thickening agents, when present, which require neutralization. The preferred amount ranges from 0.1 to 2.0% by weight, based on the total weight of the composition.

Other Optional Components

In order to confer to the cosmetic composition of the present invention some desirable characteristic that has not yet been achieved with the cited components, one may add optional components that are compatible with the properties thereof. Some of these compounds that may be added to the composition are:

bacteriostatic, bactericidal or antimicrobial compounds;
 stabilizing agents such as sodium chloride;
 dyes;
 plant extracts, plant extracts: chamomile, rosemary, thyme, calendula, carrot extract, common juniper extract, gentian extract, cucumber extract;
 optical diffusers; and
 other cosmetically accepted components that are compatible with the base composition.

Process for Preparing the Composition of the Present Invention

The preferred process for preparing the cosmetic composition of the present invention will be explained hereinafter, being based on the hot emulsification technique. This emulsifying process (at a temperature of 80° C.) is applicable to the present invention because it ensures one to obtain products having special physical-chemical properties, as for example, optimum physical-chemical stability and ability of forming liquid crystals.

The steps of the process described hereinafter are fundamental, since the formation of these structures may vary depending on the type and concentration of the emulsifiers used, as well as on the temperature employed in the process (intensity and time of heating/cooling). Thus, by carrying out the process of the present invention, one achieves the intensive and prolonged moisturizing effect desired.

The stirring of the cosmetic composition should be constant. Thus, in all the steps there should be a stirring means, that is to say, one always uses a stirrer. This stirrer may be: agitator, anchor, scraper, naval, homogenizing rotor/stator, turbine, a combination thereof or still any other means capable of keeping the cosmetic composition in question under constant stirring.

By preference, one uses as a mixer the combination of a rotor/stator type homogenizer, an agitator and a scraper. Eventually one may use a vacuum system.

The process of preparing the cosmetic composition of the present invention comprises the following steps:

f) preparing PHASE A:
  adding the wetting agent of vegetable origin, at a temperature of about 25° C. and mixing it at a frequency ranging from 20 to 2000 rpm, for a period of 3 to 10 minutes. After achieving complete solubilization and/or dispersion, heating this phase until a temperature of about 80° C. is reached;
 g) preparing PHASE B:
  solubilizing cetearyl olivate and sorbitan olivate, in at least one thermostable liquid emollient at a temperature of about 80° C., mixing them at a frequency ranging from 100 to 250 rpm;
 h) preparing PHASE C:
  promoting hot emulsification, at a temperature of about 80° C., by adding the phase B to the phase A under constant stirring of 500 to 2000 rpm;
 i) preparing PHASE E:
  adding to the phase C at least one oiliness adsorbing agent, at a temperature of about 55° C., mixing at a frequency of 20 to 1500 rpm for 3 to 8 minutes;
 j) preparing PHASE F:
  homogenizing at least one silicone with biosaccharide gum-1, at a temperature of about 25° C. at a frequency of 200 to 400 rpm;
  adding the phase F to the phase C at a temperature of about 40° C., mixing at a frequency ranging from 20 rpm to 1400 rpm until complete incorporation is achieved, that is, until the desired consistency is achieved.

Further, other components may be added to the formulation after the hot emulsification phase, as for instance, preservatives, active ingredients, essences, pH and viscosity adjusters, among others.

In order to add a preservative, for example, the process of preparing the cosmetic composition of the present invention comprises the following additional step:

Preparing PHASE D:
  adding to the phase C at least one preserving agent at a temperature of 60° C., mixing it with the aid of a scraper at a frequency of 25 rpm and a rotor/stator type homogenizer at a frequency of 1200 rpm for a period of 3 minutes.

In order to add an essence, for example, the process of preparing the cosmetic composition of the present invention comprises the following additional step:

Preparing PHASE G:
  adding to the phase C the essence at a temperature of 25° C. and mixing it with the aid of a scraper at a frequency of 20 rpm and a rotor/stator type homogenizer at a frequency of 1600 rpm for a period of about 3 minutes;

neutralizing the pH of the composition by adding a pH-adjusting agent until the physiological pH has been reached, which ranges from 4.5 to 6.5, and mixing the composition with the aid of a stirrer at a frequency of 25 rpm, a scraper at a frequency of 20 rpm and a rotor/stator type homogenizer at a frequency of 1600 rpm for a period of 5 minutes.

An example of a process of preparing the cosmetic composition of the present invention is described below:

1. To prepare phase A:

solubilizing the selected chelating agent in water (or the carrier selected for the present composition) at a temperature of 25° C., with the aid of a stirrer at a frequency of 20 rpm, a scraper at a frequency of 25 rpm and a rotor/stator type homogenizer at a frequency of 1200 rpm for 3 minutes;

adding the wetting agent of vegetable origin at a temperature of 25° C. and mixing it with the aid of a stirrer at a frequency of 20 rpm, a scraper at a frequency of 25 rpm and a rotor/stator type homogenizer at a frequency of 1200 rpm for a period of 3 minutes;

dispersing the thickening agents at a temperature of 25° C. and mixing them with the aid of a stirrer at a frequency of 20 rpm, a scraper at a frequency of 25 rpm and a rotor/stator type homogenizer at a frequency of 1400 rpm for a period of 4 minutes;

when all the components are completely dispersed, heating the phase A up to a temperature of 80° C.

2. To prepare phase B:

solubilizing the olive esters, additional emulsifying agents, co-emulsifying agents, the antioxidant agents, the waxy emollients and thermostable liquid emollients at a temperature of 80° C., and mixing them with the aid of a stirrer at a frequency ranging from 100 to 250 rpm;

keeping the mixture at the temperature of 80° C. and the frequency of stirring between 100 and 250 rpm, checking the dissolution of all the components of this phase.

3. To prepare phase C:

promoting the hot emulsification at a temperature of 80° C., by adding the phase B to the phase A;

mixing with the aid of a stirrer at a frequency of 20 rpm, a scraper at a frequency of 25 rpm and a rotor/stator type homogenizer at a frequency of 1500 rpm for a period of 2 minutes.

4. To prepare phase D:

adding to the phase C at least one preserving agent at a temperature of 60° C., mixing it with the aid of a stirrer at a frequency of 20 rpm, a scraper at a frequency of 25 rpm and a rotor/stator type homogenizer at a frequency of 1200 rpm for a period of 3 minutes.

5. To prepare phase E:

adding to the phase C at least one oiliness adsorbing agent, at a temperature of 55° C., mixing with the aid of a stirrer at a frequency of 20 rpm, a scraper at a frequency of 25 rpm and a rotor/stator type homogenizer at a frequency of 1200 rpm for a period of 5 minutes.

6. To prepare phase F:

homogenizing the compounds of the silicone system with at least biosaccharide gum-1 and optionally other skin conditioning agents, at a temperature of 25° C., with the aid of at least one stirrer at a frequency of 200 to 400 rpm;

adding the phase F to the phase C at a temperature of 40° C., mixing with the aid of a scraper at a frequency of 20 rpm and a rotor/stator type homogenizer at a frequency of 1400 rpm for a period of 4 minutes.

7. To prepare phase G:

adding to the phase C the active principles and aromatic compositions sensitive to temperature variation at a temperature of 25° C. and mixing them with the aid of a scraper at a frequency of 20 rpm and a rotor/stator homogenizer at a frequency of 1600 rpm during an interval that may last from 2 to 4 minutes;

adding active principles in the form of microcapsules at a temperature of 25° C., mixing them with the aid of a scraper at a frequency of 20 rpm and a rotor/stator type homogenizer at a frequency of 1600 rpm for a period of 3 minutes;

neutralizing the pH of the composition by adding a pH-adjusting agent until the physiological pH is reached, which ranges from 4.5 to 6.5, and mixing the composition with the aid of a stirrer at a frequency of 25 rpm, a scraper at a frequency of 20 rpm and a rotor/stator type homogenizer at a frequency of 1600 rpm for a period of 5 minutes.

Examples of the Cosmetic Composition of the Present Invention

The examples below are preferred embodiments of the cosmetic compositions of the present invention, and should not be interpreted as being limitations thereof. So, many other variations of composition may be carried out within the scope of protection delimited by the accompanying claims.

EXAMPLE 1

General Base Formula

This composition has been prepared in accordance with the process of the present invention, which comprises the following steps:

1. To prepare phase A:

solubilizing EDTA in water at a temperature of 25° C., with the aid of a stirrer at a frequency of 20 rpm, a scraper at a frequency of 25 rpm and a rotor/stator type homogenizer at a frequency of 1200 rpm for a period of 3 minutes;

adding vegetable glycerin at a temperature of 25° C., and mixing it with the aid of a stirrer at a frequency of 20 rpm, a scraper at a frequency of 25 rpm and a rotor/stator type homogenizer at a frequency of 1200 rpm for a period of 3 minutes;

dispersing the thickening agents alkyl TR-1 acrylate and xanthan gum at a temperature of 25° C. and mixing them with the aid of a stirrer at a frequency of 20 rpm, a scraper at a frequency of 25 rpm and a rotor/stator type homogenizer at a frequency of 1400 rpm for a period of 4 minutes;

when all the components are completely dispersed, heating the phase A up to a temperature of 80° C.

2. To prepare phase B:

solubilizing sorbitan olivate, cetearyl olivate, BHT, the thermostable waxy and liquid emollients, cetyl lactate, triglycerides of the capric-caprylic acid, dicaprylic ether, dicapryl carbonate and glyceryl stearate at a temperature of 80° C., and mixing them with the aid of a stirrer at a frequency ranging from 100 to 250 rpm;

keeping the mixture at a temperature of 80° C. and at the frequency of stirring between 100 and 250 rpm, checking the dissolution of all the components of this phase.

3. To prepare phase C:
promoting the hot emulsification at a temperature of 80° C., by adding the phase B to the phase A;
mixing with the aid of a stirrer at a frequency of 20 rpm, a scraper at a frequency of 25 rpm and a rotor/stator type homogenizer at a frequency of 1500 rpm for a period of 2 minutes.

4. To prepare phase D:
adding to the phase C phenoxiethanol and 3-iodo-2-propinylbutyl carbamate at a temperature of 60° C., mixing it with the aid of a stirrer at a frequency of 20 rpm, a scraper at a frequency of 25 rpm and a rotor/stator type homogenizer at a frequency of 1200 rpm for a period of 3 minutes.

5. To prepare phase E:
adding to the phase C Nylon 12, at a temperature of 55° C., mixing with the aid of a stirrer at a frequency of 20 rpm, a scraper at a frequency 25 rpm and a rotor/stator type homogenizer at a frequency of 1200 rpm for a period of 5 minutes.

6. To prepare phase F:
homogenizing the silicones cyclomethicone, crospolymer of cyclomethicone and dimethicone and dimethicone with biosaccharide gum-1 at a temperature of 25° C., with the aid of at least one stirrer at a frequency of 200 to 400 rpm;
adding the phase F to the phase C at a temperature of 40° C., mixing with the aid of a scraper at a frequency of 20 rpm and a rotor/stator type homogenizer at a frequency of 1400 rpm for a period of 4 minutes.

7. To prepare phase G:
adding to the phase C the essence at a temperature of 25° C. and mixing it with the aid of a scraper at a frequency of 20 rpm and a rotor/stator type homogenizer at a frequency of 1600 rpm for a period of 3 minutes;
neutralizing the pH of the composition, adding triethanolamine until the physiological pH is reached, which ranges from 4.5 to 6.5, and mixing the composition with the aid of a stirrer at a frequency of 25 rpm, a scraper at a frequency of 20 rpm and a rotor/stator type homogenizer at a frequency of 1600 rpm for a period of 5 minutes.

| Phase | Components | Massic composition (%) |
| --- | --- | --- |
| A | Demineralized water | qsp 100 (%) |
| A | EDTA | 0.10 |
| A | Vegetable glycerin | 5.00 |
| A | Alkyl TR-1 acrylate | 0.20 |
| A | Xanthan gum | 0.20 |
| A | Sorbitan olivate, cetearyl olivate | 4.00 |
| B | Cetyl lactate | 1.00 |
| B | Triglycerides of capric-caprylic acid | 1.00 |
| B | Dicaprylic ether | 2.00 |
| B | Dicapryl carbonate | 0.50 |
| B | Glyceryl stearate | 0.50 |
| B | BHT | 0.05 |
| D | Phenoxyethanol | 0.60 |
| D | 3-iodo-2-propinylbuthyl carbamate | 0.10 |
| E | Nylon 12 | 2.00 |
| F | Cyclomethicone | 3.00 |
| F | Crospolymer of cyclomethicone and dimethycone | 8.00 |
| F | Dimethicone | 0.10 |
| F | Biosaccharide gum-1 | 7.00 |
| G | Triethanolamine | 0.10 |
| G | Essence Inovação Mod AF ® | 0.18 |

EXAMPLE 2

Intensive Antispot Moisturizing Emulsion

To prepare this composition, one added vegetable glycerin (at a high concentration) and the active principles, biosaccharide gum 2 and 3, jambu extract, encapsulated tocoferol (Vitamin E).

| Phase | Components | Massic amount (%) |
| --- | --- | --- |
| A | Demineralized water | Qsp 100% |
| A | Vegetable glycerin | 5.00 |
| A | Crospolymer of acrylates/$C_{10-30}$ alkyl acrylate | 0.20 |
| A | Xanthan gum | 0.20 |
| A | Disodium EDTA | 0.01 |
| B | Cetearyl olivate, sorbitan olivate | 4.00 |
| B | Dicapryl ether | 2.00 |
| B | Capric/caprylic triglycerides | 1.00 |
| B | Cetyl lactate | 1.00 |
| B | Dicapryl carbonate | 0.50 |
| B | Glyceryl stearate | 0.50 |
| B | BHT | 0.05 |
| D | Phenoxyethanol | 0.60 |
| D | 3-iodo-2-propinylbutyl carbamate | 0.10 |
| E | Nylon 12 | 2.00 |
| F | Cyclomethicone and crospolymer of dimethicone | 10.00 |
| F | Biosaccharide gum-1 | 7.00 |
| F | Cyclomethicone | 3.00 |
| G | Biosaccharide gum-3 | 0.50 |
| G | Biosaccharide gum-2 | 0.50 |
| G | Fragrance | 0.18 |
| G | *Acmella oleracea* extract | 0.125 |
| G | Triethanolamine | 0.15 |
| G | Tocoferol (Vitamin E) in Talaspheres | 0.06 |

EXAMPLE 3

Nutritional Emulsion for the Eyes Area

To prepare this composition, one added the emollient Shea butter, active ingredients such as biosaccharide gums-2 and -3 and the OPC glycospheres of grape seeds and still optical diffusers such as polymethylmetacrylate titanium dioxide and copolymer of ethylene and acrylic acid.

| Phase | Components | Massic composition (%) |
| --- | --- | --- |
| A | Demineralized water | Qsp 100% |
| A | EDTA | 0.10 |
| A | Vegetable glycerin | 10.00 |
| A | TR-1 alkyl acrylate | 0.20 |
| A | Xanthan gum | 0.20 |
| B | Sorbitan olivate, cetearyl olivate | 4.00 |
| B | Cetyl lactate | 1.00 |
| B | Capric-caprylic acid triglycerides | 1.00 |
| B | Dicaprylic ether | 2.00 |
| B | Dicapryl carbonate | 0.50 |
| B | Glyceryl stearate | 0.50 |
| B | Shea butter | 3.00 |
| B | BHT | 0.05 |
| D | Phenoxyethanol | 0.60 |
| D | 3-iodo-2-propinylbutyl carbamate | 0.10 |
| E | Nylon 12 | 3.0 |
| F | Cyclomethicone | 3.00 |
| F | Crospolymer of cyclomethicone and dimethycone | 8.00 |
| F | Biosaccharide gum-1 | 8.00 |

-continued

| Phase | Components | Massic composition (%) |
|---|---|---|
| G | Triethanolamine | 9.10 |
| G | Essence Inovação Mod AF ® | 0.18 |
| G | Biosaccharide gum-2 | 0.50 |
| G | Biosaccharide gum-3 | 0.50 |
| G | Glycospheres of OPC of grape-seed | 1.00 |
| H | Copolymer of ethylene and acrylic acid | 2.00 |
| H | Polymethylmetacrylate titanium dioxide | 2.00 |

EXAMPLE 4

Body Emulsion for Dried Areas

To prepare this composition, agents that promote high emollience, such as Shea butter and cupuaçu butter, were added.

| Phase | Components | Massic composition (%) |
|---|---|---|
| Ä | Demineralized water | Qsp 100 |
| A | EDTA | 0.10 |
| A | Vegetable glycerin | 8.00 |
| A | TR-1 alkyl acrylate | 0.20 |
| A | Xanthan gum | 0.20 |
| B | Sorbitan olivate, cetearyl olivate | 4.00 |
| B | Cetyl lactate | 1.00 |
| B | Capric-caprylic acid triglycerides | 1.00 |
| B | Dicaprylic ether | 0.50 |
| B | Dicapryl carbonate | 0.50 |
| B | Glyceryl stearate | 0.50 |
| B | Shea butter | 2.00 |
| B | Cupuaçu butter | 1.50 |
| B | BHT | 0.05 |
| D | Phenoxyethanol | 0.60 |
| D | 3-iodo-2-propinylbutyl carbamate | 0.10 |
| E | Nylon 12 | 3.00 |
| F | Cyclomethicone | 3.00 |
| F | Crospolymer of cyclomethicone and dimethicone | 5.00 |
| F | Dimethicone | 1.50 |
| F | Biosaccharide gum-1 | 8.00 |
| G | Triethanolamine | 0.10 |
| G | Essence Inovação Mod AF ® | 0.18 |

Tests

1) Sensorial Evaluation of Subjective Attributes by Trained Sensorial Panel

The objective of this test is to identify the sensorial profile of the product. The term "sensorial" should be understood to mean a set of properties: brightness, fatty film, velvety film and spreadability.

The descriptive analysis is one of the most common sensorial methodologies used for surveying the qualitative and quantitative (intensity) sensorial aspects of a product. In this method, one requires from the volunteer the description of a product in terms of its sensorial characteristics and the respective quantification of the intensity of each cited characteristic, by using scales for this purpose.

The following model has been used: from 10 to 15 qualified evaluators always coordinated by a panel leader, who is a facilitator for the development of the sensorial language. The panel was formed as follows: recruiting the evaluators, developing the descriptive terminology, training and selection, sensory testing (descriptive capacity, reproducibility and individual consensus with the team) and analysis of the results.

The following materials have been used: micropipettes, products from the competitors, reference materials for intensity scale of the respective attributes evaluated, physiological serum (control) and absorbent paper.

The procedure followed, with the panel being validated (after training and calibration), followed the steps below:

the female volunteers evaluated the attributes descried in TABLE 01, using an evaluation index card and the quantitative references described in this card. The female volunteers evaluated the products at random, in three repetitions.

TABLE 01

Sensorial attributes of products for skin care:

| Descriptive term | Definition of the terminology |
|---|---|
| Absorption point | Number of rotations necessary for the product to start being absorbed by the skin |
| Spreadability | Ease to spread/spread the product over the skin |
| Sliding | Ease to slide/slide the finger over the skin |
| Brightness of the skin | Intensity of reflected light on the skin |
| Stickiness | Intensity with which a finger adheres to the skin |
| Oiliness | Feeling of oil on the skin upon spreading the product |
| Fatty film | Feeling of fat, forming a film on the skin, after spreading the product |
| Velvety film | Feeling of "skin like a peach" |

The products were evaluated in 5-cm-diameter circular sites in the forearm region, two fingers away from the wrists and two fingers away from the elbows. The amount of product applied to each site is of 25 µl, spread in rotation, obeying the rhythm of the metronome at the speed of 120 pulses per minute.

To evaluate the attributes, the following methodologies have been used:

absorption point: one applies the product at one of the circular sites and observes the number of rotations necessary for the product to start being absorbed by the skin;

other attributes: one applies the product at one of the circular sites and makes 15 rotations to spread it and effect the evaluations.

The products tested in the present test were:

Product 1—the composition described in example 2;

Product 2—composition: water, cyclohexasyloxane, glycerin, mineral oil, Nylon-66, myristyl myristate, dipropylene glycol, stearic acid, palmitic acid, PEG-100 stearate, glyceryl stearate, lithium silicate and sodium magnesium, drometrizole, trisiloxane, ethylhexyl metocynnamate, peg-20 stearate, tocoferyl acetate, cetyl alcohol, stearyl alcohol, triethanolamine, polyacryloyldimethyl ammonium taurate, *Boswellia serrata* extract, manganese glyconate, phenoxyethanol, imidazolidinic urea, methyl paraben and fragrance.

Product 3—composition: water, cyclopentasiloxane, glycerin, cyclomethicone, glycolic acid, 2-ethylhexyl p-methoxycinnamate, ammonium hydroxide, propyleneglycol, crospolymer of dimethicone/vinyl dimethicone, trioxaundecanedioic acid, dimethicone copolyol, methicone cetearyl, *Punica granatum* juice, cetyl dimethicone copolymer, sodium chloride, benzyl alcohol, silica, perfume, paraffin, 1,3 butanediol, *Cocos nucifera* juice, manitol, hydrolyzed wheat protein, glycogen, *Daucus carota sativa* root extract, *Olea europea* leaf extract, *Pyrus malus* root extract, yeast extract, *Panax ginseng* root extract, *Padina pavonica* extract, *Tilia cordata* xylem extract, *Aesculus hippocastanum* seed extract, *Foeniculum vulgare* (fennel) fruit extract, *Mendicago sativa* fruit extract, *Saccharomyces* yeast filtrate, *Peptona*

*pichia* filtrate, peg-40 hydrogenated caster oil, talcum, biotin, calcium pantotenate, methicone and dyes; and Product 4—composition: water, cyclopentasiloxane, *Butyrospermum parkii*, Shea Butter fruit, glycerin, isohexadecane, *Zea mays*, maize starch, silica, pentaerythrityl tetraethylhexanoate, white wax, beeswax, stearic acid, palmitic acid, PEG-100 stearate, glyceryl stearate, Peg-20 stearate, Big-Peg-18 Methyl Ether Dimethyl Silane, stearyl alcohol, *Prunus armeniaca*, apricot kernel oil, Peg-4 dilaurate, Peg-4 laurate, soybean glycine, soybean oil, dimethiconol, manganese sulfate, methylparaben, PCA arginin, adenosine, magnesium sulfate, disodium EDTA, tocoferol, dipotassium glycyrrhizate, iodopropinylbutylcarbamate, capryl glycol, hydrolyzed algin, copolymer of acryloyldimethyltaurate acrylamide/sodium, butylparaben, polysorbate 80, benzophenone-4 and scent.

The data obtained are shown in the table below:

|  | Brightness | Fatty film | Velvety film | Spreadability |
|---|---|---|---|---|
| Product 1 | 1.1 | 0.6 | 5.0 | 6.9 |
| Product 2 | 2.8 | 2.0 | 4.5 | 5.6 |
| Product 3 | 4.6 | 2.2 | 4.8 | 5.4 |
| Product 4 | 2.6 | 1.4 | 4.9 | 5.3 |

Result: from the analysis of the tables presented one can conclude that the sensorial of the cosmetic composition of the present invention is the most favorable one.

One can observe, in a clear way, that the cosmetic composition of the present invention was the product that, after application onto the skin, exhibited less brightness and fatty film, these characteristics being totally undesirable. In addition, with regard to the velvety film left, one observes that the cosmetic composition of the present invention confers to the skin an extremely pleasant sensorial, contributing to the increase in softness. Finally, with regard to the spreadability, one observes that the cosmetic composition of the present invention exhibits high values, suggesting that in the moment of application the consumer will have an unequal well-being sensation, without his skin becoming oily or sticky.

It is pointed out that the sensory analysis by a trained panel considers other attributes, like the absorption point, sliding, stickiness and oiliness of the products. In short, the cosmetic composition of the present invention has exhibited optimum performance in all the cited attributes, being considered the best product in comparison with other tested products from competitors.

One has also carried out evaluation tests by the consumer/user and also clinical studies so as to prove the efficacy and safety of the cosmetic composition of the present invention. Further information on the cited tests is given below:

2) Evaluation by the Consumers after Prolonged Use of the Cosmetic Composition

This study aims at evaluating the acceptance of the cosmetic composition of the present invention by the consumer, and the evaluation was effected together with the clinical safety study described later.

180 female volunteers with age between 35 and 65 were selected having facial aging spots confirmed in the clinical evaluation. The exclusion criteria comprised: pregnancy/lactation, use of anti-inflammatory/immunosuppressive drugs, atopic/allergic backgrounds, active diseases of the skin that may interfere with the results of the study, endocrine diseases such at thyroid-related diseases, diabetes, ovarian or adrenal-gland disorders, a background indicating reaction to cosmetic products for the face area, intensive exposure to sunlight of up to 15 days before the evaluation, active skin lesions in the evaluation area, esthetic treatments up to 3 weeks before the selection, dermatological treatments up to 3 months before the selection, background indicating inefficacy and/or reactions to the products being tested.

The volunteers discussed the sensations, benefits and desired characteristics with the application of a cosmetic product like this one. The discussion was supervised by experts in the area and, right afterwards, an e-evaluation questionnaire for performance and acceptance of the product was handed out and answered during the testing period. The results below show the percentage of volunteers who perceived an improvement in the attributes after 15 days of use of each product tested.

Result: the acceptance by the volunteers was very high, after 15 days of use of the product, considering the following attributes, among others: moisturizing, softness, general appearance and freshness of the skin.

3) Clinical Evaluation after Prolonged Use of the Cosmetic Composition 3.1) Clinical Study of Efficacy Considering the same panel of female volunteers, exclusion criteria and attributes described above, the dermatologist evaluated the women's skins along 15 days of use of the products being tested and came to the following conclusion:

After 15 days: one observed the increase in softness, moisturizing, improvement in the general appearance of the skin and reduction of parching and aging of the skin.

3.2) Clinical, Monoblind, Randomized, Controlled Study of the Potential of Irritability, Sensitization, Phototoxicity and Photoallergy of the Skin This study has the function of evaluating adverse reactions that may be caused with application of the cosmetic composition to the skin. By adverse reactions one understands any signal or symptom triggered by a topical product used correctly. As examples of adverse reactions, one can cite: contact eczematous dermatitis, urticaria, acne and patches.

The irritation potential of a product depends on a number of variables: the components of the composition, the concentration of each of the components, absorption thereof by the skin, the amount applied to the skin, the state in which the skin is at the time of application, the mode and frequency of application of the product to the skin and the inherent cumulative effect of the product.

The patch test is the main tool used in diagnosing the reaction caused by a cosmetic and in the research on allergenicity. In the research on allergenicity the following clinical tests are involved: primary and accumulated dermal irritability, sensitization of the skin, phototoxicity and photoallergy. These consist on repeated applications of the product to the skin and they have the function of detecting possible irritations or induction of sensitization. It is advisable to carry out tests of use after approval of the product in the patch tests. With the tests of use, one can evaluate, in addition to allergenicity, sensorial characteristics of the products, that is to say, their performance.

In order to carry out the allergenicity tests, 137 volunteers of both sexes were selected (132 women and 5 men), of all races, with age ranging from 18 to 67 years, excluding subjects that had dermatological diseases, lesions or nerve on the dorsum and were pregnant or nursing.

For effecting this study, one has used the following material: a hypoallergenic adhesive patch for patch test with discs of filter paper of 1.0 cm$^2$, duly identified, hypoallergenic semipermeable sticking-plaster for occlusion, a saline solution and samples of the cosmetic composition. One applied 0.05 g of the cosmetic composition to each 1-cm$^2$ area of the disc of filter paper, and to the control disc one applied the saline solution. These discs were fixed to the dorsum of the volunteers with the aid of sticking-plaster.

The following clinical researches have also been carried out:

I. Research on Primary Irritability

The testing method used was the patch test or the epicutaneous test (occlusive patch test). The sites of application of the tests were the dorsum of the volunteers, duly protected. The patch test was removed by the researchers after 48 hours of contact with the skin and the reactions were written down, 30 minutes after removal.

II. Research on Accumulated Irritability

The sample was applied always in the same region, on the dorsum, duly protected. The applications were effected every day, the patch test remaining 72 hours in the weekend, for 4 consecutive weeks, in a total of 20 applications. The sample was re-applied onto the skin always at the same place and the reactions were written down. After 20 consecutive applications, a rest period of 10 days followed, when no plaster was applied. After this rest interval, a simple plaster of sample was applied to the dorsum of the volunteers, virgin area, that is to say, a place where no plaster had been applied. The test was removed by the researchers after 48 hours of contact with the skin, and the reactions were written down, 30 minutes after removal.

III. Research on Sensitization

The sample was applied always in the same region of the dorsum duly protected. The applications were carried out 3 times a week for 3 consecutive weeks, on alternating days, resulting in a total of 9 applications. The patch test was removed by the researches 24 hours after application thereof. After a series of 9 consecutive applications, a 10-day rest period followed, when no plaster was applied. Then, a simple plaster of the sample was applied to the dorsum of the volunteers, in the virgin area. The patch test was removed by the researchers after 48 hours of contact with the skin, and the reactions were written down, 30 minutes after removal.

IV. Research of Phototoxicity and Photoallergy

By phototoxicity one understands the increase in skin reactivity to ultraviolet light without immunological base, and by photoallergy one understands the increase in skin reactivity to ultraviolet light with immunological base.

The test was carried out as follows: the cosmetic composition was applied to the dorsum of the volunteers at a concentration of $0.05 \, g/cm^2$, always protected. The applications were effected twice a week for 3 weeks, resulting in a total of 6 applications. The patch test was removed by the researchers 24 hours after application, the area being immediately evaluated and irradiated with ultraviolet A and B lamp. The non-irradiated areas of the dorsum and the eyes were duly protected from incidence of light. The sample was reapplied always at the same place. After 6 consecutive applications and irradiations, a 10-day rest period followed, when no plaster and no irradiation were effected. Then, a plaster was applied to the dorsum of the volunteers, in the virgin area. The tests were removed by the researchers after 48 hours from application. After removal, the test areas were irradiated with UVA/UVB lamp. The volunteers were instructed to protect the irradiated area from the sunlight. Evaluations were carried out 24 and 48 hours after the last irradiation and written down in a form for this purpose.

RESULTS: The products did not induce any skin irritation or sensitization process and did not cause phototoxicity or photoallergy, during the study period.

3.3) Monoblind, Clinical Study of Tolerability of the Skin and of the Eye Region, in Real Conditions of Use of the Product This study was worked out to determine the prevalence of adverse reactions in real conditions of use and to evaluate the comedogenicity potential of the product. 90 female volunteers with age between 30 and 65 years were selected for individual test of the products, considering the following exclusion criteria: pregnancy/lactation, use of anti-inflammatory/immunosuppressive drugs, atopic/allergic backgrounds, active diseases of the skin that may interfere with the results of the study, endocrine diseases such at thyroid-related diseases, diabetes, ovarian or adrenal-gland disorders, a background indicating reaction to cosmetic products for the face area, intensive exposure to sunlight of up to 15 days before the evaluation, active skin lesions in the evaluation area, esthetic treatments up to 3 weeks before the selection, dermatological treatments up to 3 months before the selection, background indicating inefficacy and/or reactions to the products being tested. The volunteers used the cosmetic composition for 30 days. Clinical evaluations on the $1^{st}, 7^{th}, 14^{th}, 28^{th}$ days of the study period were scheduled.

RESULTS:

in real conditions of use, according to the frequency and the mode of application determined, no volunteer presented any skin or eye lesion related to the product. Further, it was observed a significant reduction of closed comedones and open comedones throughout the study.

3.4) Study of Prolonged Moisturizing Kinetics by Corneometry

This study aims at evaluating the moisturizing potential of the cosmetic composition of the present invention. For this study one used: a corneometer that measures the water content in the skin, specifying the degree of moisturizing of the skin surface. One selected volunteers who were instructed not to use any cosmetic product on their forearms during the three days prior to the beginning of the test. The product was applied to determined 1-$cm^2$ areas of the forearms in an amount of 2 mg. One of the areas is kept without product. The measurements of the corneometer are carried out in the beginning of the test and 2, 15, 18 and 24 hours after application of the product to the skin. All these measurements are effected in a specific room (moisturizing room), where the temperature and humidity are kept constant (temperature of 22° C. and maximum relative humidity of 55%).

RESULTS: according to this test, it was possible to prove that the cosmetic compositions in question promoted moisturizing of the skin, evidenced by an increase in the corneometry, in the times 2, 15, 18 and 24 hours, with respect to the control.

4) Evaluation of the Cosmetic Composition of the Present Invention with Respect to Products of Competitors The objective of the following tests is to evaluate the cosmetic composition of the present invention with respect to products of competitors for different attributes and requirements.

The products evaluated are the products 1, 3 and 4 described in test 1.

This test was divided into the following assays:
quantitative study with personal and domiciliary interviews;
blind test with pure monadic evaluation;
time of use being 7 days with the use of the product at least 5 times a week.

540 female volunteers were selected, with ages ranging from 30 to 45 years, from social class A and B1, who used anti-spot products at least 5 times a weak, with oily, mixed and normal skin, not being pregnant or nursing.

The composition of each block of evaluation is reproduced below:

| Panel | Age | | Type of skin | | Social class | |
|---|---|---|---|---|---|---|
| | 30-37 | 38-45 | Oily/mixed | Normal | A | B1 |
| Product 1 | 73 | 107 | 90 | 90 | 90 | 90 |
| Product 3 | 72 | 108 | 90 | 90 | 90 | 90 |
| Product 4 | 75 | 105 | 90 | 90 | 90 | 90 | a. Spontaneous Evaluation of the Tested Product

| | Product 1 | Product 3 | Product 4 |
|---|---|---|---|
| They liked it | 74% | 61% | 70% |
| They did not like it | 2% | 4% | 2% |
| They did not know how to answer | 24% | 34% | 28 |

Therefore, one notes that the cosmetic composition of the present invention was considered better in comparison with products from the competitors. The main reasons that led the volunteers to this conclusion are listed below:

it provides moisturizing;
  it is smooth;
  it has a pleasant scent;
  it is not fatty, does not leave the skin oily;
  it penetrates the skin and is well absorbed therein;
  it treats, protects and cares for the skin;
  it does not leave the skin with brightness;
  it spreads, slides well on the skin;
  it has fast absorption;
  it refreshes the skin;
  it does not cause allergy.

b. Evaluation of the Product Tested on a Generic Scale

| Opinion of the volunteers | Very satisfied | Satisfied |
|---|---|---|
| Product 1 | 36% | 51% |
| Product 3 | 27% | 52% |
| Product 4 | 30% | 57% | c. General Evaluation

| Opinion of the volunteers | Mark 10 | Mark 9 |
|---|---|---|
| Product 1 | 40% | 23% |
| Product 3 | 33% | 21% |
| Product 4 | 28% | 29% | d. Test for Rapidity of Absorption

| Opinion of the volunteers | It absorbs in the ideal way, as I like it |
|---|---|
| Product 1 | 92% |
| Product 3 | 77% |
| Product 4 | 86% | e. Evaluation of Attributes (% of Opinions "Optimum")

| Attributes | Product 1 (%) | Product 3 (%) | Product 4 (%) |
|---|---|---|---|
| Having adequate consistency | 58 | 53 | 52 |
| Moisturizing the skin | 60 | 56 | 55 |
| Does not leave a feeling of oily skin | 61 | 44 | 53 |
| Being easy to spread | 78 | 62 | 65 |
| Having pleasant scent | 65 | 43 | 50 |
| Exhibiting easy absorption | 69 | 48 | 54 |
| Leaving the skin soft/silky | 67 | 59 | 56 |
| Leaving the skin fresh/alive | 61 | 52 | 50 |
| Leaving the skin beautiful | 59 | 46 | 44 |
| Having light/soft texture | 64 | 51 | 56 |
| Does not irritate the skin/does not cause itching | 73 | 68 | 68 |
| Leaving the skin with a natural look | 54 | 48 | 48 |

From the result of all the tests described above, one can conclude that the cosmetic composition of the present invention has proved to be quite superior when compared with the products from the competitors.

The invention claimed is:

1. A cosmetic composition consisting essentially of:
    a mixture of cetearyl olivate and sorbitan olivate;
    biosaccharide gum-1;
    at least one wetting agent of vegetable origin;
    at least one emollient of vegetable origin;
    at least one silicone; and
    at least one oiliness adsorbent.

2. A cosmetic composition according to claim 1, wherein the mixture of cetearyl olivate and sorbitan olivate is present in an amount ranging from 2.0% to 10.0% by weight, based on the total weight of the composition.

3. A cosmetic composition according to claim 2, wherein the mixture of cetearyl olivate and sorbitan olivate is present in an amount of about 4.0% by weight, based on the total weight of the composition.

4. A cosmetic composition according to claim 1, wherein the biosaccharide gum-1 is present in an amount ranging from 3.0% to 10.0% by weight, based on the total weight of the composition.

5. A cosmetic composition according to claim 4, wherein the biosaccharide gum-1 is present in an amount of about 8.0% by weight, based on the total weight of the composition.

6. A cosmetic composition according to claim 1, wherein the at least one wetting agent of vegetable origin is present in an amount ranging from 2.0% to 10.0% by weight, based on the total weight of the composition.

7. A cosmetic composition according to claim 6, characterized in that the wetting agent is vegetable glycerin, which is present in the composition in an amount ranging from 5.0% to 10.0% by weight, based on the total weight of the composition.

8. A cosmetic composition according to claim 1, wherein the at least one emollient in an amount ranging from 2.5% to 44.0% by weight, based on the total weight of the composition.

9. A cosmetic composition according to claim 8, characterized in that the emollient is present in an amount of about 4.5% by weight, based on the total weight of the composition and is selected from the group consisting of cetyl lactate, triglycerides of capric and caprylic acid, dicaprylic ether, dicapryl carbonate and combinations thereof.

10. A cosmetic composition according to claim 1, wherein the at least one silicone is present in an amount ranging from 1.6% to 50.0% by weight, based on the total weight of the composition.

11. A cosmetic composition according to claim 10, characterized in that the silicone is present in an amount of about 11.5% by weight, based on the total weight of the composition and is selected from: cyclomethicone, crospolymer of cyclomethicone and dimethicone, dimethicone and combinations thereof.

12. A cosmetic composition according to claim 1, wherein the at least one oiliness adsorber is present in an amount ranging from 0.1% to 5.0% by weight, based on the total weight of the composition.

13. A cosmetic composition according to claim 12, characterized in that the oiliness adsorber is Nylon and is present in an amount of about 3.0% by weight, based on the total weight of the composition.

14. A process of preparing a cosmetic composition consisting essentially of the following steps:
   a) preparing a PHASE A
      adding a wetting agent of vegetable origin, at a temperature of about 25° C., and mixing it at a frequency ranging from 20 to 2000 rpm, for a period of 3 to 10 minutes; after achieving complete solubilization and/or dispersion, heating said PHASE A until a temperature of about 80° C. is reached;
   b) preparing a PHASE B:
      solubilizing cetearyl olivate and sorbitan olivate, in at least one thermostable liquid emollient at a temperature of about 80° C., mixing them at a frequency ranging from 100 to 250 rpm;
   c) preparing a PHASE C:
      promoting hot emulsification, at a temperature of about 80° C., by adding the PHASE B to the PHASE A under constant stirring of 500 to 2000 rpm;
   d) preparing a PHASE E:
      adding to the PHASE C at least one oiliness adsorbing agent, at a temperature of about 55° C., mixing at a frequency of 20 to 1500 rpm for a period of 3 to 8 minutes;
   e) preparing a PHASE F:
      homogenizing at least one silicone with biosaccharide gum-1, at a temperature of about 25° C. at a frequency of 200 to 400 rpm;
      adding the PHASE F to the PHASE E at a temperature of about 40° C., mixing at a frequency ranging from 20 rpm to 1400 rpm.

15. A process according to claim 14, further comprising the steps of adding to the PHASE C at least one preserving agent at a temperature of 60° C., mixing it with the aid of a scraper at a frequency of 25 rpm and a rotor/stator type homogenizer at a frequency of 1200 rpm for a period of 3 minutes.

16. A process according to claim 14 further comprising the steps of adding to the PHASE C an essence at a temperature of 25° C. and mixing it with the aid of a scraper at a frequency of 20 rpm and a rotor/stator type homogenizer at a frequency of 1600 rpm for a period of about 3 minutes;
   neutralizing the pH by adding a pH-adjusting agent until the pH ranges from 4.5 to 6.5, and mixing with the aid of a stirrer at a frequency of 25 rpm, a scraper at a frequency of 20 rpm and a rotor/stator type homogenizer at a frequency of 1600 rpm for a period of 5 minutes.

17. A cosmetic product characterized by comprising the cosmetic composition as defined in claim 1.

18. A composition consisting essentially of:
   a mixture of cetearyl olivate and sorbitan olivate, wherein the mixture of cetearyl olivate and sorbitan olivate is present in an amount ranging from 2.0% to 10.0% by weight, based on the total weight of the composition;
   biosaccharide gum-1 that is present in an amount ranging from 3.0% to 10.0% by weight, based on the total weight of the composition;
   at least one wetting agent of vegetable origin that is present in an amount ranging from 2.0% to 10.0% by weight, based on the total weight of the composition;
   at least one emollient of vegetable origin that is present in an amount ranging from 2.5% to 44.0% by weight, based on the total weight of the composition and being selected from the group consisting of cetyl lactate, triglycerides of capric and caprylic acid, dicaprylic ether, dicapryl carbonate and combinations thereof;
   at least one silicone that is present in an amount ranging from 1.6% to 50.0% by weight, based on the total weight of the composition and being selected from the group consisting of cyclomethicone, crospolymer of cyclomethicone and dimethicone, dimethicone and combinations thereof; and
   at least one oiliness adsorbent that is present in an amount ranging from 0.1% to 5.0% by weight, based on the total weight of the composition.

19. The composition of claim 18, wherein the wetting agent is vegetable glycerin, which is present in the composition in an amount ranging from 5.0% to 10.0% by weight, based on the total weight of the composition.

20. The composition of claim 19, wherein the oiliness adsorber is Nylon and is present in an amount of about 3.0% by weight, based on the total weight of the composition.

* * * * *

UNITED STATES PATENT AND TRADEMARK OFFICE
CERTIFICATE OF CORRECTION

PATENT NO. : 8,158,111 B2  
APPLICATION NO. : 11/917271  
DATED : April 17, 2012  
INVENTOR(S) : Roberto et al.

Page 1 of 1

It is certified that error appears in the above-identified patent and that said Letters Patent is hereby corrected as shown below:

<u>Title page,</u>

(22) PCT Filed: "Sep. 7, 2006" should read --Sep. 8, 2006--;

(30) Foreign Application Priority Data,

"Sep. 9, 2005 (BR) ..........0503719" should read

--Sep. 9, 2005 (BR) ..........P1-0503719-0--.

Signed and Sealed this  
Eighteenth Day of December, 2012

David J. Kappos  
*Director of the United States Patent and Trademark Office*